United States Patent
Middlebrooks et al.

(10) Patent No.: US 10,810,739 B2
(45) Date of Patent: Oct. 20, 2020

(54) PROGRAMMATIC QUALITY ASSESSMENT OF IMAGES

(71) Applicant: University of Florida Research Foundation, Inc., Gainesville, FL (US)

(72) Inventors: Erik Hayden Middlebrooks, Gainesville, FL (US); Mohit Rana, Gainesville, FL (US); Alissa M. Old Crow, Gainesville, FL (US); Jake Rieke, Gainesville, FL (US); Ranganatha Sitaram, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 293 days.

(21) Appl. No.: 16/070,407

(22) PCT Filed: Jan. 20, 2017

(86) PCT No.: PCT/US2017/014268
§ 371 (c)(1),
(2) Date: Jul. 16, 2018

(87) PCT Pub. No.: WO2017/127633
PCT Pub. Date: Jul. 27, 2017

(65) Prior Publication Data
US 2019/0066297 A1    Feb. 28, 2019

Related U.S. Application Data

(60) Provisional application No. 62/281,030, filed on Jan. 20, 2016.

(51) Int. Cl.
*A61B 5/05*    (2006.01)
*G06K 9/00*    (2006.01)
(Continued)

(52) U.S. Cl.
CPC .......... *G06T 7/0016* (2013.01); *A61B 5/0013* (2013.01); *A61B 5/055* (2013.01);
(Continued)

(58) Field of Classification Search
USPC ....... 382/100, 103, 106, 128–133, 154, 162, 382/172, 173, 181, 219, 224, 254, 276,
(Continued)

(56) References Cited

U.S. PATENT DOCUMENTS 7,432,706 B2    10/2008    Van Der Kouwe
8,055,041 B2    11/2011    Mazaika et al.
(Continued)

FOREIGN PATENT DOCUMENTS

| | | |
|---|---|---|
| CN | 103279644 A | 9/2013 |
| WO | WO 2007/047915 A2 | 4/2007 |
| WO | WO 2007/126610 A2 | 11/2007 |

OTHER PUBLICATIONS

GE Healthcare, "Magnetic Resonance Imaging | GE Healthcare", retrieved from <https://www.gehealthcare.com/en/products/magnetic-resonance-imaging> (formerly https://www3.gehealthcare.com/en/Products/Categories/Magnetic-Resonance-Imaging), retrieved on Dec. 18, 2018, 5 pages.

(Continued)

*Primary Examiner* — Seyed H Azarian
(74) *Attorney, Agent, or Firm* — Alston & Bird LLP

(57) ABSTRACT

Example embodiments provide real time quality monitoring of a magnetic resonance imaging (MRI) scan. Data associated with an MRI scan of a particular patient is received. The data is sequential MRI data associated with various times. A rate of change of the sequential data is determined with reference to the various times. It is determined whether the rate of change of the sequential data meets a first configurable threshold. It is determined whether the rate of change (Continued)

of the sequential data meets a second configurable threshold. The sequential data is classified based on whether the rate of change of the sequential data meets the first and second configurable thresholds.

16 Claims, 9 Drawing Sheets

(51) Int. Cl.
    *G06T 7/00*         (2017.01)
    *A61B 5/055*       (2006.01)
    *A61B 5/00*         (2006.01)
    *G01R 33/56*       (2006.01)
    *G06F 19/00*       (2018.01)
    *G06T 7/269*       (2017.01)
    *G06T 7/246*       (2017.01)
    *G16H 30/40*       (2018.01)
    *G01R 33/54*       (2006.01)
    *G16H 40/20*       (2018.01)
    *G16H 40/63*       (2018.01)
(52) U.S. Cl.
    CPC .......... *A61B 5/7207* (2013.01); *A61B 5/7264* (2013.01); *G01R 33/546* (2013.01); *G01R 33/5608* (2013.01); *G06F 19/34* (2013.01); *G06T 7/248* (2017.01); *G06T 7/269* (2017.01); *G16H 30/40* (2018.01); *A61B 5/7239* (2013.01); *A61B 2576/00* (2013.01); *G06T 2207/10088* (2013.01); *G06T 2207/30004* (2013.01); *G06T 2207/30168* (2013.01); *G16H 40/20* (2018.01); *G16H 40/63* (2018.01)
(58) Field of Classification Search
    USPC ....... 382/285, 291, 305; 378/4, 21; 600/410, 600/413; 324/309
    See application file for complete search history.

(56) References Cited

U.S. PATENT DOCUMENTS

| | | |
|---|---|---|
| 8,191,359 B2 | 6/2012 | White et al. |
| 8,390,291 B2 | 3/2013 | Macfarlane et al. |
| 2004/0171927 A1 | 9/2004 | Lowen et al. |
| 2007/0165927 A1* | 7/2007 | Muradyan ............... G06T 5/002 382/128 |
| 2012/0010495 A1* | 1/2012 | de Oliveira .......... G01R 33/543 600/410 |
| 2014/0064586 A1* | 3/2014 | Peacock, III ........ A61B 5/4566 382/131 |
| 2014/0111199 A1 | 4/2014 | Oh et al. |
| 2014/0343399 A1* | 11/2014 | Posse ..................... A61B 5/055 600/410 |
| 2015/0091569 A1* | 4/2015 | Shinoda ............... G01R 33/543 324/309 |
| 2015/0257660 A1* | 9/2015 | Miyazaki ............. A61B 5/0263 600/413 |

OTHER PUBLICATIONS

Jones, T., B., et al., "Integration of Motion Correction and Physiological Noise Regression in fMRI", NeuroImage, Aug. 15, 2008 (available online May 21, 2008), pp. 582-590, vol. 42, Issue 2, Elsevier Inc.

Koush, Y., et al., "Signal Quality and Bayesian Signal Processing in Neurofeedback Based on Real-Time fMRI", NeuroImage, Jan. 2, 2012 (available online Aug. 4, 2011), vol. 59, Issue 1, pp. 478-489, Elsevier Inc.

Philips, "MRI Systems & Solutions | Philips Healthcare", retrieved from <https://www.usa.philips.com/healthcare/solutions/magnetic-resonance> on Dec. 18, 2018, 7 pages.

Siemens Healthcare USA, "Magnetic Resonance Imaging", Apr. 24, 2013 to Nov. 16, 2018, Internet Archive <https://web.archive.org/web/20130424081030/https://usa.healthcare.siemens.com/magnetic-resonance-imaging>, 2 pages, retrieved Dec. 18, 2018.

Sulzer, J., et al., "Real-Time fMRI Neurofeedback: Progress and Challenges", NeuroImage, Aug. 1, 2013 (available online Mar. 27, 2013), pp. 386-399, vol. 76, Elsevier Inc.

Toshiba America Medical Systems, "Magnetic Resonance Imaging | Toshiba America Medical Systems", Jun. 19, 2014 to Feb. 1, 2018, Internet Archive <https://web.archive.org/web/20140619002326/http://medical.toshiba.com/products/mr/>, 2 pages, retrieved on Dec. 18, 2018.

Weiskopf, Nikolaus, et al., "Real-Time Functional Magnetic Resonance Imaging: Methods and Applications", Magnetic Resonance Imaging, Jul. 2007, pp. 989-1003, vol. 25, Elsevier, Inc.

International Searching Authority, International Search Report and Written Opinion for International Application No. PCT/US2017/014268, dated May 18, 2017, 13 pages, Korean Intellectual Property Office, Republic of Korean.

* cited by examiner

PROGRAMMATIC QUALITY ASSESSMENT OF IMAGES

CROSS REFERENCE TO RELATED APPLICATIONS

This application is a National Stage Application, filed under 35 U.S.C. 371, of International Application No. PCT/US2017/014268, filed Jan. 20, 2017, which claims priority to U.S. Application No. 62/281,030, filed Jan. 20, 2016; the contents of both of which are hereby incorporated by reference in their entirety.

BACKGROUND

A plurality of factors and features may be used to determine quality of magnetic resonance imaging (MRI) data. Applicant has identified a number of deficiencies and problems associated with determining the quality of time-dependent MRI data. Through applied effort, ingenuity, and innovation, many of these identified problems have been solved by developing solutions that are included in embodiments of the present invention, many examples of which are described in detail herein.

BRIEF SUMMARY

This specification relates to quality assessments of MRI data. In some implementations, the quality is determined based on a unique set of parameters identified by the inventors. In one implementation, the set of parameters include spatial average of voxel intensity over a region of interest (ROI), averaged across time divided by the temporal standard deviation of the spatial mean in the ROIs, after de-trending is applied to the time series. In some implementations, the parameters further include signal to noise ratio, signal to fluctuation noise ratio, signal to ghost ratio, head displacement, global intensity average, and variance for a respective four-dimensional data set.

Particular embodiments of the subject matter described herein can be implemented so as to realize one or more of the following advantages: allow for providing real-time indications of the quality of MRI scans which can be used to guide management of patients receiving MRI scans; provide a more accurate estimate of the quality of scans and allows for determination of whether a patient needs to restart an MRI scan and/or make adjustments to improve the quality of the MRI scan; eliminate unnecessary MRI scans in real time or near real time and in turn reduce the resources required for MRI scans and improve the user experience of patients.

According to one aspect of the present invention a computer implemented method for providing real time quality monitoring of a magnetic resonance imaging (MRI) scan is provided. In an example embodiment, the method comprises receiving data associated with an MRI scan of a particular patient, the data being sequential MRI data associated with various times. The method may further comprise determining a rate of change of the sequential data with reference to the various times; determining whether the rate of change of the sequential data meets a first configurable threshold; and determining whether the rate of change of the sequential data meets a second configurable threshold. The method may further comprise classifying the sequential data based on whether the rate of change of the sequential data meets the first and second configurable thresholds.

According to another aspect of the present invention, a computer implemented method for real time quality monitoring of a magnetic resonance imaging (MRI) scan is provided. In an example embodiment, the method comprises receiving a three dimensional data set, the three dimensional data set representing a plurality of intensity measurements, each intensity measurement being associated with a time and a spatial location; and determining, a measure of quality for the received three-dimensional data set based on one or more parameters, wherein determining the one or more parameters comprises determining a variance for the three dimensional data set.

The details of one or more embodiments of the subject matter described herein are set forth in the accompanying drawings and the description below. Other features, aspects, and advantages of the subject matter will become apparent from the description, the drawings, and the claims.

BRIEF DESCRIPTION OF THE FIGURES

Figure 1:
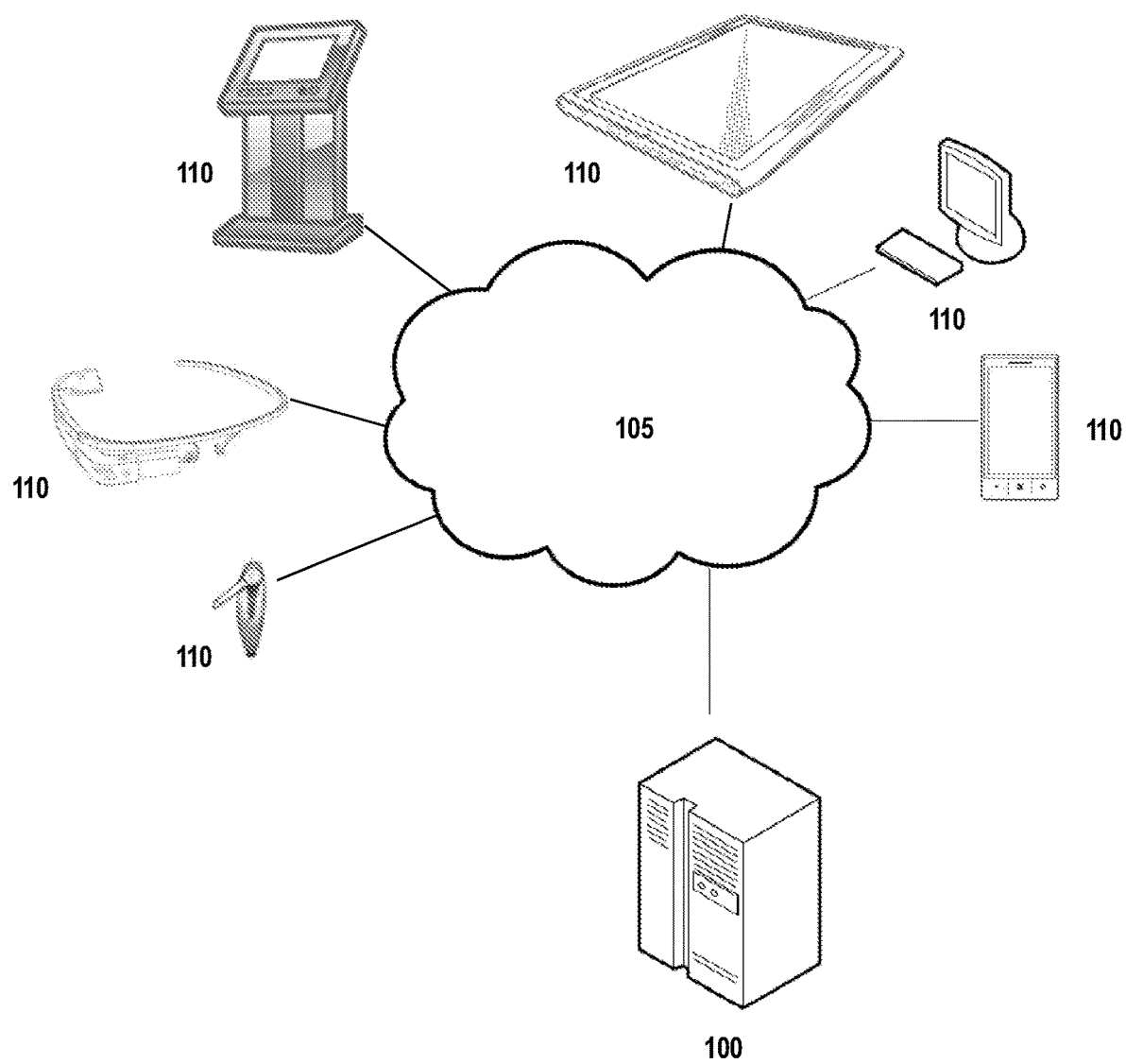
Figure 2:
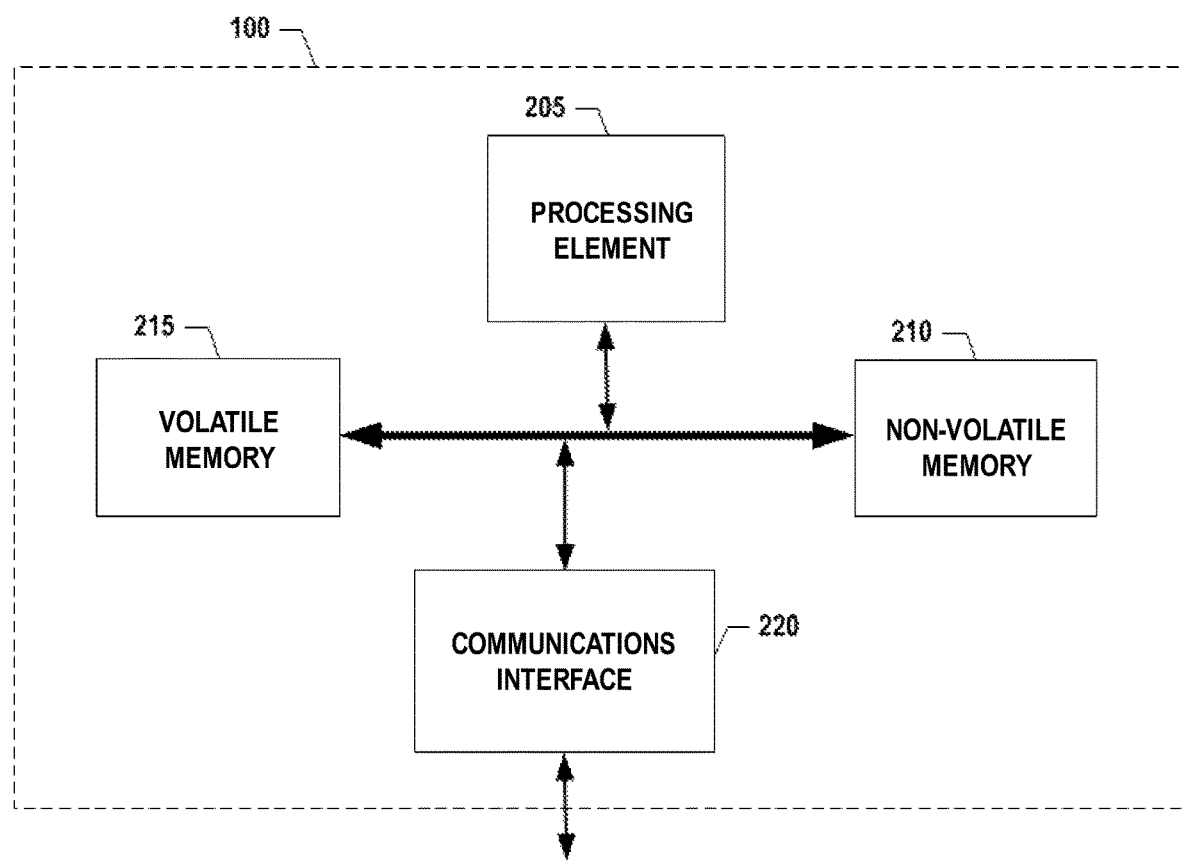
Figure 3:
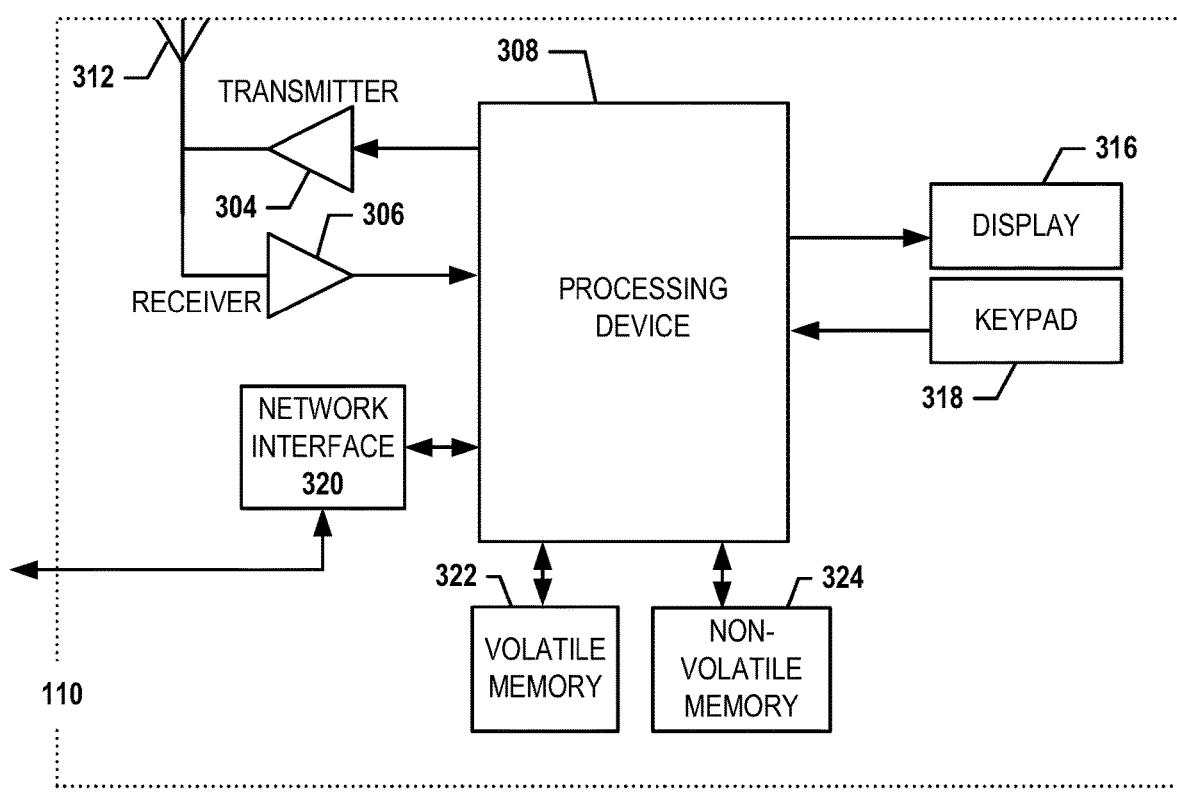
Figure 4:
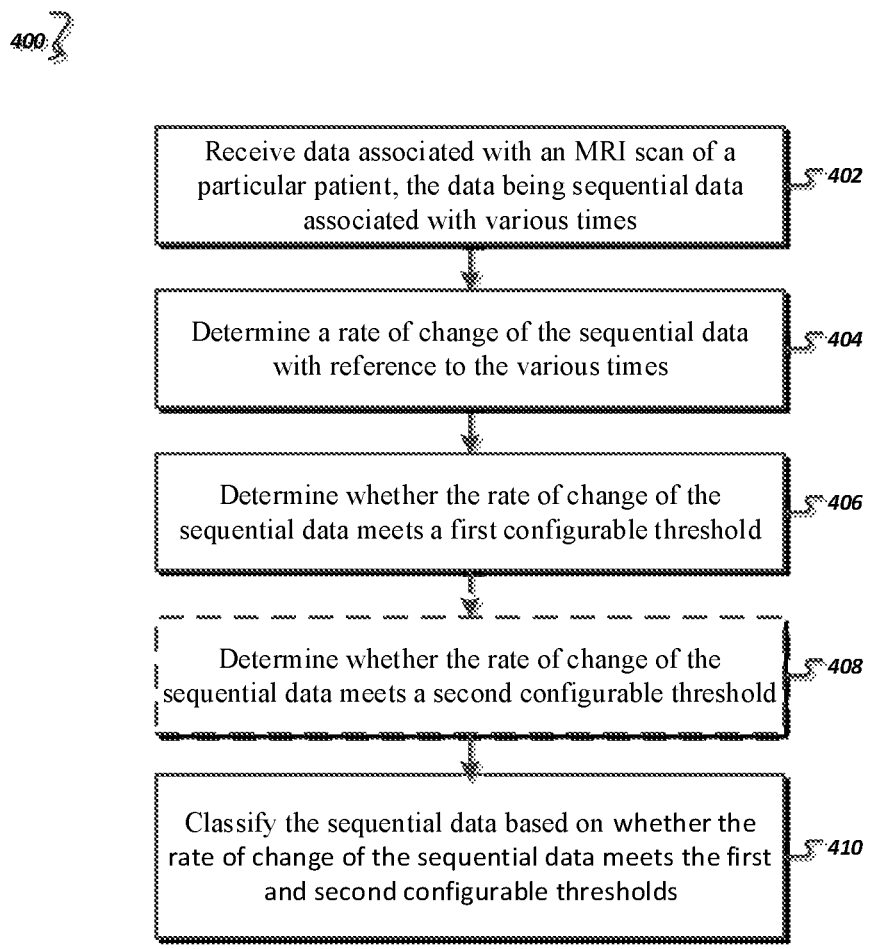
Figure 5:
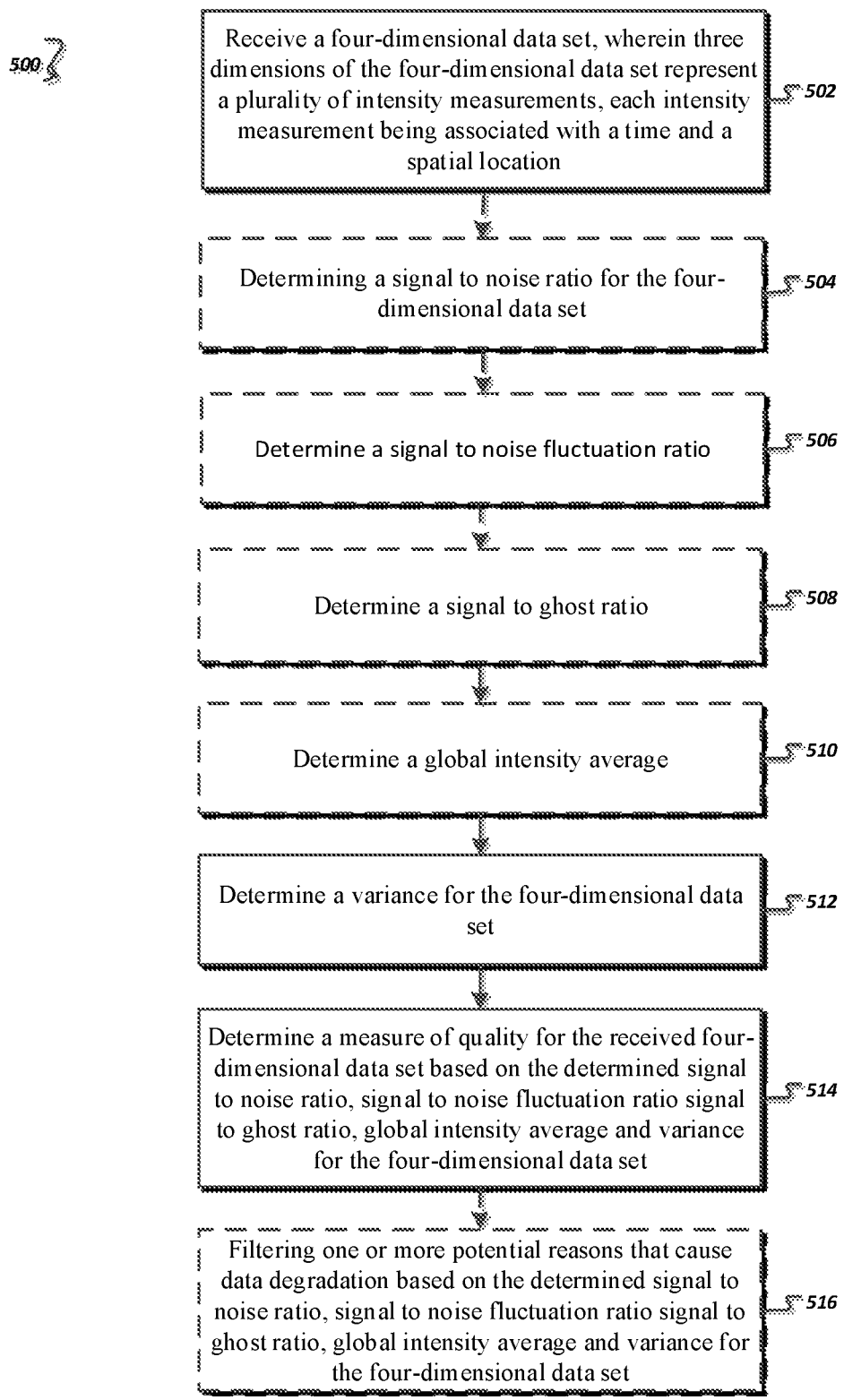
Figure 6:
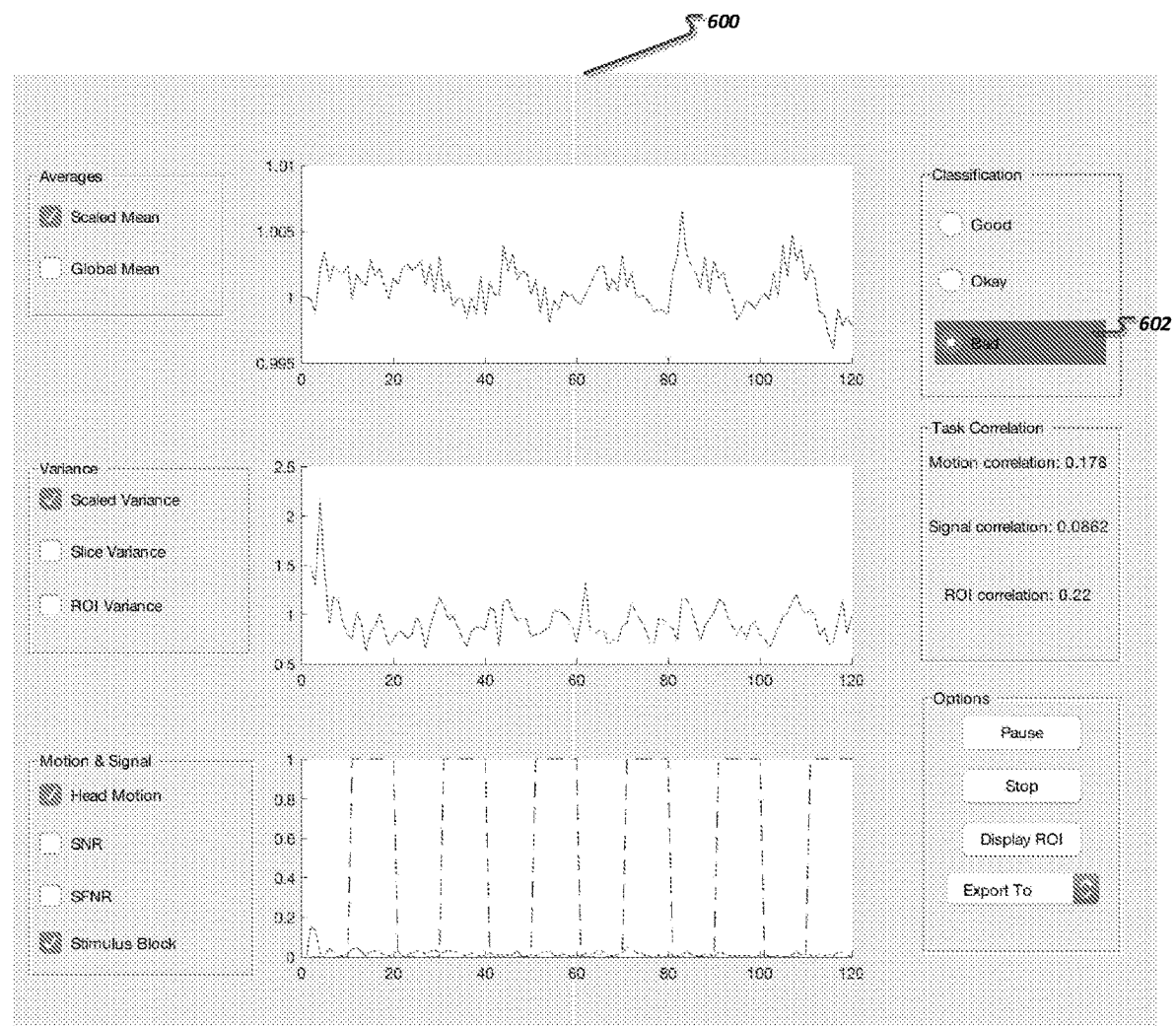
Figure 7A:
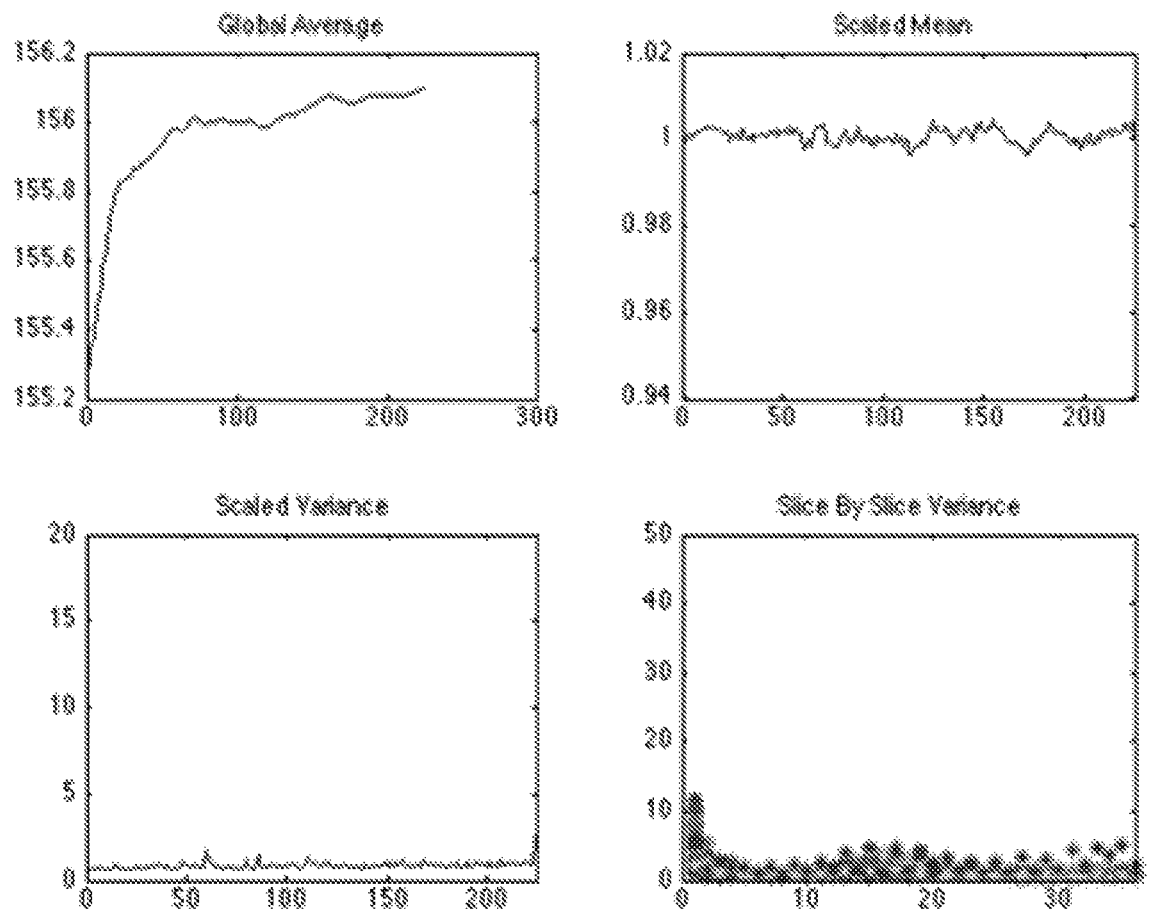
Figure 7B:
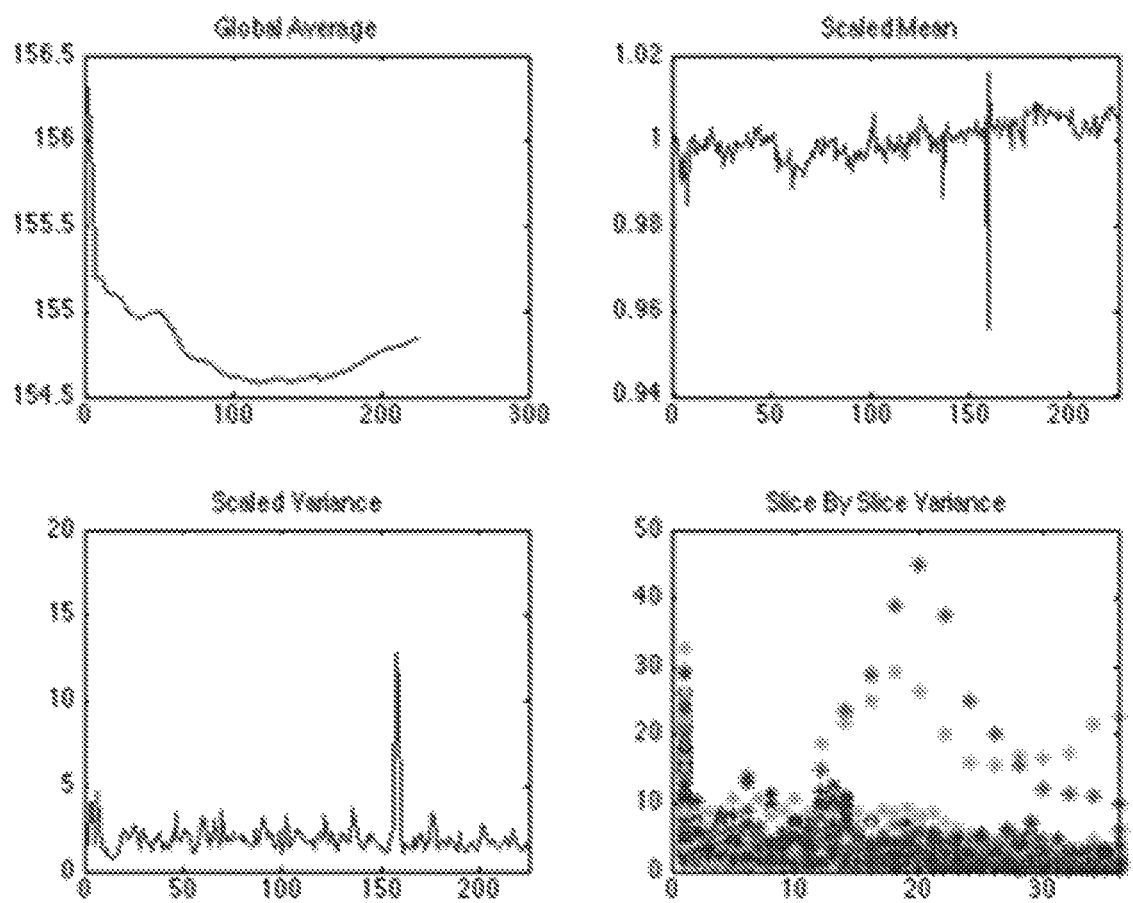
Figure 7C:
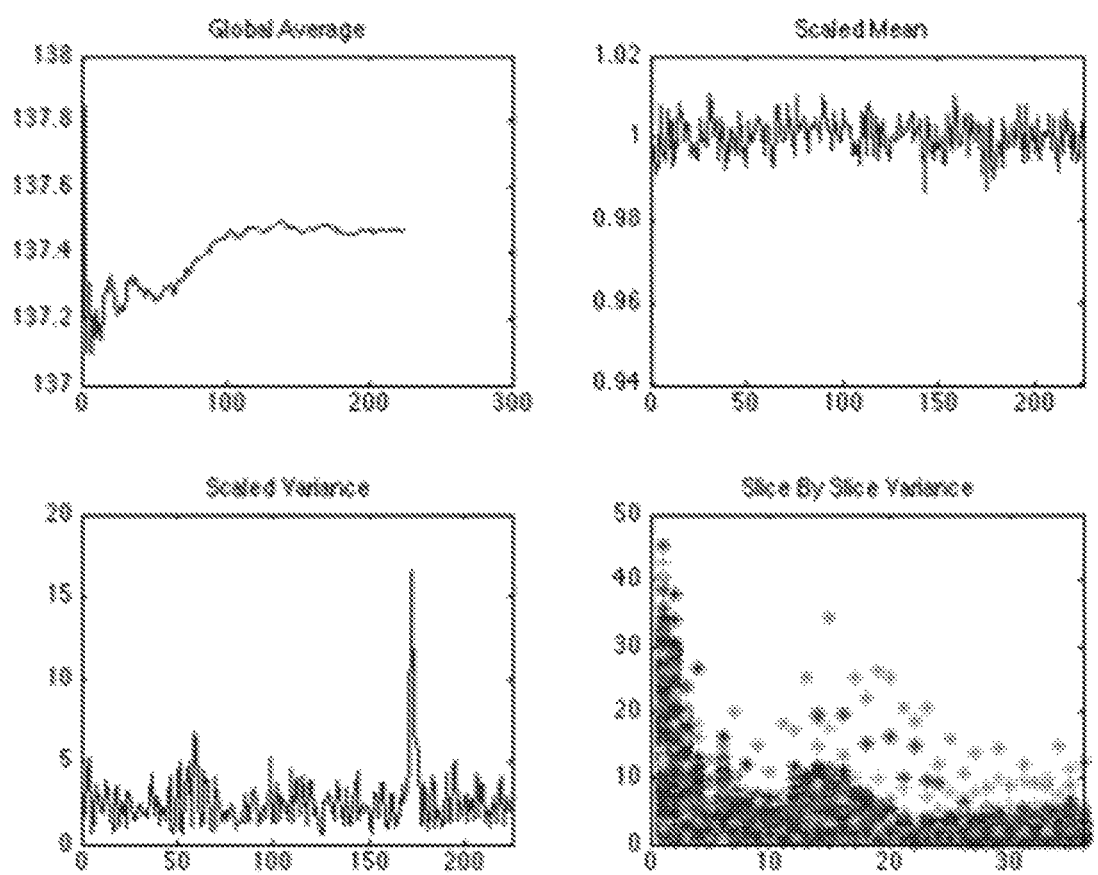

Having thus described the invention in general terms, reference will now be made to the accompanying drawings, which are not necessarily drawn to scale, and wherein:

FIG. 1 is an overview of a system that can be used to practice embodiments of the present invention;

FIG. 2 is an exemplary schematic diagram of a management computing entity according to one embodiment of the present invention;

FIG. 3 is an exemplary schematic diagram of a user computing entity according to one embodiment of the present invention;

FIGS. 4 and 5 are flow charts illustrating various exemplary procedures and operations that may be completed in accordance with various embodiments of the present invention;

FIG. 6 illustrates an example user interface that may be provided indicating a classification of the quality of the data; and FIGS. 7A-7C illustrates exemplary data sets associated with different scan qualities.

DETAILED DESCRIPTION OF VARIOUS EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of an exemplary embodiment of the present invention. As shown in FIG. 1, this particular embodiment may include one or more assessment computing entities 100, one or more networks 105, and one or more user computing entities 110. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

1. Exemplary Assessment Computing Entity

FIG. 2 provides a schematic of an assessment computing entity 100 according to one embodiment of the present invention. An assessment computing entity 100 may belong to, a medical facility, hospital, clinic, diagnostic service, and/or the like. However, the assessment computing entity 100 may belong a third party computing service that performs remote computations for a medical facility. In general, the terms computing entity, computer, entity, device, system, and/or similar words used herein interchangeably may refer to, for example, one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the assessment computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. For instance, the assessment computing entity 100 may communicate with user computing entities 110 and/or a variety of other computing entities.

As shown in FIG. 2, in one embodiment, the assessment computing entity 100 may include or be in communication with one or more processing elements 205 (also referred to as processors, processing circuitry, and/or similar terms used herein interchangeably) that communicate with other elements within the assessment computing entity 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the assessment computing entity 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like.

The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the assessment computing entity 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the assessment computing entity 100 with the assistance of the processing element 205 and operating system.

As indicated, in one embodiment, the assessment computing entity 100 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the assessment computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown, the assessment computing entity 100 may include or be in communication with one or more input elements, such as a keyboard input, a mouse input, a touch screen/display input, motion input, movement input, audio input, pointing device input, joystick input, keypad input, and/or the like. The assessment computing entity 100 may also include or be in communication with one or more output elements (not shown), such as audio output, video output, screen/display output, motion output, movement output, and/or the like.

As will be appreciated, one or more of the assessment computing entity's 100 components may be located remotely from other assessment computing entity 100 components, such as in a distributed system. Furthermore, one or more of the components may be combined and additional components performing functions described herein may be included in the assessment computing entity 100. Thus, the assessment computing entity 100 can be adapted to accommodate a variety of needs and circumstances. As will be recognized, these architectures and descriptions are provided for exemplary purposes only and are not limiting to the various embodiments.

2. Exemplary User Computing Entity

A user may be an individual, a family, a company, an organization, an entity, a department within an organization, a representative of an organization and/or person, and/or the like. In one example, users may be medical personnel, doctors, nurses, patients, and/or the like. For instance, a user may operate a user computing entity 110 that includes one or more components that are functionally similar to those of the assessment computing entity 100. FIG. 3 provides an illustrative schematic representative of a user computing entity 110 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, gaming consoles (e.g., Xbox, Play Station, Wii), watches, glasses, key fobs, radio frequency identification (RFID) tags, ear pieces, scanners, cameras, wristbands, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 110 can be operated by various parties. As shown in FIG. 3, the user computing entity 110 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the user computing entity 110 may be capable of operating with one or more air interface standards, communication protocols, modulation types, and access types. More particularly, the user computing entity 110 may operate in accordance with any of a number of wireless communication standards and protocols, such as those described above with regard to the assessment computing entity 100. In a particular embodiment, the user computing entity 110 may operate in accordance with multiple wireless communication standards and protocols, such as UMTS, CDMA2000, 1xRTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 110 may operate in accordance with multiple wired communication standards and protocols, such as those described above with regard to the assessment computing entity 100 via a network interface 320.

Via these communication standards and protocols, the user computing entity 110 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 110 can also download changes, add-ons, and updates, for instance, to its firmware, software (e.g., including executable instructions, applications, program modules), and operating system.

According to one embodiment, the user computing entity 110 may include location determining aspects, devices, modules, functionalities, and/or similar words used herein interchangeably. For example, the user computing entity 110 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's 110 position in connection with a variety of other systems, including cellular towers, Wi-Fi access points, and/or the like. Similarly, the user computing entity 110 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 110 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the user computing entity 110 to interact with and/or cause display of information from the assessment computing entity 100, as described herein. The user input interface can comprise any of a number of devices or interfaces allowing the user computing entity 110 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the user computing entity 110 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 110 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 110. As indicated, this may include a user application that is resident on the entity or accessible through a browser or other user interface for communicating with the assessment computing entity 100 and/or various other computing entities.

In another embodiment, the user computing entity 110 may include one or more components or functionality that are the same or similar to those of the assessment computing entity 100, as described in greater detail above. As will be recognized, these architectures and descriptions are provided for exemplary purposes only and are not limiting to the various embodiments.

III. EXEMPLARY SYSTEM OPERATION

Example embodiments provide a solution to the technical problem of obtaining quality data from an MRI or other scan. In particular, during a scan various artifacts may be introduced into the data set during the performance of the scan. The introduction of these artifacts may not be obvious in real time or near real time as the scan is taking place. However, after the scan, when the data is analyzed and/or post-processed, the artifacts may become apparent and the data set may be unusable. Thus, it is important to be able to determine in real time and/or near real time (e.g., during the scan) if the data set being obtained contains artifacts that would make the data set unusable. Example embodiments monitor various parameters of the data set as the data set is being obtained (e.g., in real time, near real time, during the scan, and/or the like). One or more parameters may be monitored using a network (e.g., neural network, deep net, and/or the like) that has been trained using a fuzzy logic supervised machine learning technique to analyze the relationships between the various parameters to determine if artifacts are present in the data set as the data set is being obtained (e.g., in real time, near real time, during the scan, and/or the like). Feedback regarding the quality of the data set being obtained may then be provided. Based on the provided feedback, the scan may continue to completion, be paused/restarted with modifications made to prevent additional/future artifacts, canceled, rescheduled, and/or the like. Thus, example embodiments prevent the waste of time, resources, and/or the like of obtaining data sets through a scan that cannot be used due to various, uncorrectable artifacts present within the data set.

According to various embodiments, the assessment computing entity 100 and/or user computing entity 110 provide and/or aid in the access of quality assessments of images or scans. The term "image" is used generically to refer to a variety of images that can be generated from various imaging techniques and processes. The imaging techniques and processes may include, for instance, fluoroscopy, magnetic resonance imaging (MRI), photoacoustic imaging, positron emission tomography (PET), projection radiography, computed axial tomography (CT scan), and ultrasound. As indicated, the images can be of a human body or one or more parts of the human body, but the images can also be of other organisms or objects. A "volume of images" or "volume" refers to a sequence of images that can be spatially related and assembled into a rectilinear block representing a dimensional region of patient anatomy. Although the following is described in the context of MRI scans, embodiments of the present invention are not limited to this context.

In one embodiment, a user interface may be accessible from a user computing entity 110 (e.g., in communication with the assessment computing entity 100 via the network 105). For example, in various embodiments, a user may log in to the assessment computing entity 100 from a user computing entity 110 (e.g., by opening a log-in page and entering a user ID and password using display 316 and keypad 318). The assessment computing entity 100 may be configured to recognize any such log-in request, verify that user has permission to access the system (e.g., by confirming the user ID and password are valid), and present/provide the user with a user interface (e.g., displayed on display 316). In other embodiments, user log-in is not required to access the user interface.

Generally, patient motion is a well-known problem associated with MRI scans. It has been estimated that an individual hospital could lose over $500,000 per year due simply to non-diagnostic studies from patient motion. Minuscule amounts of motion, which are imperceptible to the human eye, can often result in corrupted and/or non-satisfactory data and/or scans. Unfortunately, such data corruption is typically discovered once the scan is complete and the patient is no longer available. In one example, a method for classifying MRI scans according to quality is provided to remedy these problems. In some implementations, the MRI scans are functional MRI scans or FMRI scans.

In one embodiment, the assessment computing entity 100 utilizes real-time data processing to continually monitor for patient motion and a host of common imaging artifacts which could render data unusable. The assessment computing entity 100 may evaluate the data in real-time and provide easy-to-understand feedback to the user regarding the cumulative data quality. Some embodiments of the invention incorporate novel quality analysis techniques to provide real-time feedback to users regarding the quality of MRI scans. In some embodiments, the quality assessment device may be incorporated into an MRI scanning device. Alternatively, the quality assessment device may be at a remote location and in direct communication with the MRI scanning device.

In some implementations, assessment computing entity 100 evaluates head displacements of users during MRI scans. In some implementations, assessment computing entity 100 evaluates other parameters to provide more accurate quality assessments. For example, assessment computing entity 100 may evaluate the spatial average of voxel intensity over a region of interest (ROI), averaged across time divided by the temporal standard deviation of the spatial mean in the ROIs, after quadratic de-trending is applied to the time series. In some embodiments, users may receive simple color-coded feedback (e.g., red, yellow, green) specifying an overall quality associated with an MRI scan based on, at least, a configurable threshold. In some implementations, the configurable threshold may be determined based on global data. For example, the configurable threshold may be determined based on mean global intensity calculated from the average spatial intensity of each volume (3D image) averaged across time. In some implementations, 3D rigid body registration may be used to determine displacement of the head across time. In some implementations, the configurable threshold may be determined based on data associated with a particular scan. In other implementations, the configurable threshold may be configured by the user.

Embodiments of the invention provide clinical decision support to help physicians, medical personnel, and patients obtain high quality MRI scans. For example, embodiments of the invention may be used by physicians, medical personnel, and patients to obtain an accurate MRI scan. Embodiments of the invention also improve the user experience for physicians, medical personnel, and patients.

FIG. 4 is a flow chart illustrating an exemplary processes 400 for classifying MRI scans in accordance with embodiments of the invention. Process 400 begins with receiving data associated with an MRI scan of a particular patient, the data being sequential data associated with various times (402). In some implementations, the process 400 may receive real time data associated with the MRI scan of the particular patient. For example, the sequential data may be a four-dimensional matrix associated with an MRI image and/or scan. The matrix may be associated with multiple variables. For example, the four-dimensional matrix may provide intensity measurements associated with different locations of a patient's brain in a three-dimensional space across multiple time points. In some implementations, the matrix may be a fifth-dimensional matrix, a sixth-dimensional matrix, and/or the like.

The process 400 continues with determining a rate of change of the sequential data with reference to the various times (404). For example, the sequential data may comprise a four dimensional data set comprising a measured and/or received intensity at a plurality of spatial points at various times. For example, the assessment computing entity 100 may determine the temporal or time derivative of the received sequential data. For example, the temporal or time derivative of the received sequential data may be determined pixel-by-pixel. For example, a first intensity of a particular pixel corresponding to a first time and a second intensity at the particular pixel corresponding to a second time may be used to determine a rate of change between the portion of the sequential data captured at the first time and the portion of the sequential data captured at the second time. This process may be completed for each pixel and/or a subset of the pixels. In an example embodiment, the average of the pixel-by-pixel rate of change may be determined. In another example embodiment, an average intensity for the portion of the sequential data set captured at the first time (or a subset thereof) may be compared to an average intensity for the portion of the sequential data set captured at the second time (or a subset thereof) to determine the rate of change of the sequential data. Various techniques may be used to determine the rate of change of the intensity of the sequential data.

The process 400 then determines whether the rate of change of the sequential data meets a first configurable threshold (406). For example, the assessment computing entity 100 may determine if the rate of change of the sequential data meets the first configurable threshold. For example, the first configurable threshold may be a threshold specifying a rate of change of sequential data below which the sequential data is considered satisfactory, high quality and/or the like. In some embodiments, the first threshold may be determined based on a variance measure for the data. In some implementations, the variance measure for the data may be a signal variance from the intensity difference between a current and a previous volumes. In some implementations, the variance measure may be the difference squared and divided by the cumulative global average. Likewise, this can be calculated by each individual slice rather than averaging over the entire volume. In an example embodiment, if the rate of change indicates an intensity change of greater than 5%, for example, it may be determined that the sequential data is not of high quality, not satisfactory, and/or the like and if the rate of change indicates an intensity change of less than or approximately 5%, for example, it may be determined that the sequential data is of high quality, satisfactory, and/or the like.

The process 400 may then continue with determining whether the rate of change of the sequential data meets a second configurable threshold (408). For example, the assessment computing entity 100 may determine whether the rate of change of the sequential data meets a second configurable threshold. For example, the second specified threshold may be the signal-to-noise ratio (SNR) calculated by the spatial average of voxel intensity over a region of interest (ROI) divided by the standard deviation (across space) of the background signal. In embodiments where analysis is performed in real time or near real time, a cumulative average is calculated across time for the "signal" and "noise" components. The SNR may then be updated with each new volume that is read-in to the program.

The process 400 may end with classifying the sequential data based on whether the rate of change of the sequential data meets the first and second configurable thresholds (410). For example, responsive to determining that the values of the rate of change are above the first configurable threshold, the assessment computing entity 100 may classify the sequential data and/or an associated MRI scan as satisfactory, high quality and/or the like. Similarly, responsive to determining that values of the rate of change are below the second configurable threshold, the assessment computing entity 100 may classify the sequential data and/or an associated MRI scan as non-satisfactory, low quality and/or the like. However, responsive to determining that values of the of the rate of change of sequential data are below the second configurable threshold and above the first configurable threshold, the assessment computing entity 100 may classify the sequential data and/or an associated MRI scan as potentially-satisfactory, average quality and/or the like. In some implementations, the classification may be performed continuously in real-time. In some embodiments, a notification or alert may be presented to assessment device 100 and/or user device 110 indicating a quality of a current MRI scan. In an example embodiment, the notification may be provided by a light source such as an LED indicator light (e.g., disposed on the control panel of the scanner and/or the like), on a display device (e.g., a user interface of the assessment computing entity 100, the display 316, and/or the like), and/or through some other display/indicator means. In some implementations, the indications may be provided continuously. For example, a green light may indicate good and/or high quality scans. A yellow light may indicate an average or a mediocre scan. A red light may indicate a low quality or bad scan. The lights may be provided to a user device continuously. For example, a green light may be shown for a first period of the MRI scan. An interference may be experienced during a second period of the scan. Accordingly, the green light may then turn red responsive to the interference. In some implementations, once the interference stops, the light may then return to green again. Accordingly, an operator is provided with notifications indicating the quality of the scan in real time or near real time during the scan.

Accordingly, operators (e.g., physicians, medical personnel, nurses) will be alerted in real time or near real time as the scan is being acquired if there is a data quality issue. Operators can then end the scan to prevent continued waste of valuable scanner time and/or attempt to better immobilize or counsel the patient on the importance of remaining still. In one implementation, an operators may receive alerts at quality assessment device 100. In some implementations, the quality assessment device 100 is part of an MRI scanning device. In some implementations, an operators may receive alerts at user device 110. In some implementations, the alerts for user device 110 may be transmitted from quality assessment device 100.

FIG. 5 is an exemplary process 500 for determining a quality measure for an MRI scan. In general, the process 500 may be performed by the assessment device 100 and/or user device 110. The process 500 begins with receiving a four-dimensional data set, three dimensions of the four-dimension data set represent a plurality of intensity measurements of the brain, each intensity measurement being associated with a time and a spatial location (502). For example, the assessment device 100 may receive a four-dimensional data set, wherein three dimensions of the four-dimension data set represent a plurality of intensity measurements of the brain, each intensity measurement being associated with a time and a spatial location. In some implementations, the matrix may be a fifth-dimensional matrix, a sixth-dimensional matrix and/or the like.

The process 500 may continue with optional step 504 shown in phantom. The process 500 may determine a signal to noise (SNR) ratio for the data set (504). For example, the assessment computing entity 100 may determine an SNR for the data set. With reference to SNR, the signal refers to the spatial average of voxel intensity over a region of interest (ROI), averaged across time. Noise refers to the standard deviation (across space) of the background signal averaged across time. In embodiments where analysis is performed in real time or near real time, a cumulative average across time for the "signal" and "noise" components is calculated. The SNR may be updated with each new volume that is read-in to the program. In particular, a rate of change may of the SNR may be determined. In an example embodiment, the rate of change of SNR may be a spatial rate of change across a portion of the sequential data captured at approximately the same time. In another example embodiment, the rate of change of the SNR may be a temporal rate of change between portions of the sequential data captured at different times. The process 500 then continues with determining head displacement across time utilizing a 3D rigid body registration.

The process 500 may then optionally continue with determining a signal to fluctuation noise ratio (SFNR) (506). For example, the assessment computing entity 100 may determine a SFNR for the received data set. With reference to SFNR, the signal is similar to the signal of the SNR. The fluctuation noise refers to the temporal standard deviation of the spatial mean in the ROIs, after de-trending is applied to the time series. The purpose of de-trending is to remove low frequency signal drift, often originating from the MR scanner or physiological noise. In general, as the scan proceeds, the operational behavior of the scanner and/or various hardware components of the scanner may change. For example, as the scanner and/or various hardware components of the scanner heat up during the operation of the scanner, the operational behavior of those components may change slightly. A de-trending is applied to account for the behavior changes of the scanner and/or various hardware components of the scanner during the operation of the scanner. In some implementations, the de-trending is quadratic de-trending. The de-trended signal is obtained by subtracting the modeled signal from the original signal. The modeled signal may be determined based on the expected change in the operational behavior of the scanner and/or various hardware components thereof. For example, the modeled signal may be determined based on the expected low frequency signal drift. The SFNR may then be calculated after a threshold of scans (e.g., 8 scans) and updated incrementally for every new volume acquired.

The process 500 may continue with determining a signal to ghost ratio (508). For example, the assessment computing entity 100 may determine an SGR for the received data set. For example, the signal to ghost ratio (SGR) may determine a ratio of the signal at the center of a patient's brain over the average signal in a background area outside the brain. The SGR may be calculated in a manner similar to the above. The process 500 may continue with optional step 512 shown in phantom. The process 500 may determine a global intensity average for the three-dimensional data set (510). In some implementations, the mean global intensity can be calculated as the average spatial intensity of each volume (3D image) averaged across time. The mean global intensity is helpful for visualizing any obvious acquisition errors. In real-time embodiments, a cumulative approach when calculating the global mean may be used. A cumulative moving average (CMA) may be calculated as follows:

$$CMA_{n+1} = \frac{x_{n+1} + n \cdot CMA_n}{n+1},$$

wherein $x_{n+1}$ is the new data from the n+1 scan, n is the number of previous scans, and $CMA_n$ is the cumulative moving average after n scans. A scaled mean of blood-oxygen-level dependent (BOLD) intensity may be calculated by determining the average intensity of each volume and dividing it by the global mean. Accordingly, each volume is normalized by the cumulative mean, which allows for comparisons across multiple sessions and provides a better visualization of signal drift.

In some implementations, the global average may be determined based on data sets from a plurality of patients. In some implementations, the global average may be update frequently and/or continuously.

The process 500 then continues with determining the signal variance from the intensity difference between the current and last volume, and squaring that difference. For example, the assessment computing entity 100 may determine the signal variance from the intensity difference between the current and last volume, and square that difference. The scaled variance is determined when the signal variance is divided by the cumulative global average. The slice-to-slice variance, which is calculated the same way as signal variance may also be considered. However, each slice may be considered separately instead of averaging the slices over the entire volume. In some implementations, the process 500 may determine the standard deviation of the three dimensional data set in lieu of determining the variance.

In general, various parameters of an MRI scan may be scanner dependent and may change from one scanner to another. Thus, the parameters considered to determine a measure of quality of the received data indicate temporal or spatial changes throughout the scan. For example, the temporal or spatial rate of change of intensity, temporal rate of change of the SNR, temporal rate of change of the SFNR, temporal rate of change of the SGR, temporal rate of change of global intensity average, temporal rate of change of patient's head displacement, and/or the like. In an example, embodiment, the time steps between consecutive scans are generally consistent throughout the scan and the change between scans (e.g., the variance) is determined rather than a rate of change. For example, the SNR is expected to be fairly consistent throughout the set of scans. Therefore, if the SNR is changing significantly between scans, the quality of the received data is likely to be low.

The process 500 may continue with determining a measure of quality for the received data set based on the determined signal to noise ratio, signal to fluctuation noise ratio, signal to ghost ratio, head displacement, global intensity average and variance for the four-dimensional data set (514). For example, the assessment computing entity 100 may determine a measure of quality for the received data set. In some implementations, the determination may be based on one or more of the parameters above. In some implementations, the process 500 may determine a rate of change threshold below which associated data and MRI scans are deemed unsatisfactory. In some embodiments, the threshold may be determined based on a variance for the data. In some implementations, the threshold may be determined based on a global mean for the data. In some embodiments, the threshold may be proportional to variance and/or the global average. In some embodiments, determining a measure of quality is based on a machine learning algorithm. The parameters above may be used as attributes for training a machine learning model.

In general, the relationships between the various parameters and the corresponding variances and/or rates of change are quite complex. In particular, when we attempted to assign weights to the various parameters, the corresponding variances and/or rates of change based on our expertise in the field, the resulting quality measure was not sufficiently predictive of the quality of the data set. Therefore, we identified the problem that relationship between the various parameters and corresponding variances and/or rates of change are too complex to manually determine a predictive model. Thus, we invented the technical solution described herein. In an example embodiment the technical solution includes using a fuzzy logic machine learning process starting without a bias (e.g., the neural network, deep net, and/or the like is not biased toward any particular weighting scheme for the variances and/or rates of change).

It should be understood that the selection and weight assignment of attributes or parameters for training machine learning models can greatly affect the respective performance. For example, statistical measures may be used as features (independent variables) to build a model for predicting data quality (0=bad, 1=good). However, in cases when quality is not so clearly delineated, a regression algorithm or a fuzzy logic approach may be used to obtain a degree of data quality. Fuzzy logic is a multivalued logical system, which can relate classes of objects with unclear boundaries in which class membership is a matter of degree. The guiding principle behind methods like fuzzy logic is to exploit the tolerance for imprecision and uncertainty to achieve a robust and low-cost solution. These systems are useful because they are conceptually straightforward, tolerant of imprecise data, and can model nonlinear functions. Fuzzy inference is the process of creating a mapping from an input space (e.g., our statistical measures such as the parameters, variances, and/or rates of change described above) to an output space (e.g., data quality [0,1]). The mapping provides basis for future decisions or classifications. The basic structure of a fuzzy system begins with accepting a number of inputs, which are used to evaluate a number of parallel rules. The rules have an if-then structure, and will be determined after analyzing several runs with our statistical measures. In some embodiments, a result of each rule is combined to determine if the system behavior is dominated by either one rule or another.

In some implementations, attributes, parameters, variances, and/or rates of change are selected and assigned weights based on the statistical analysis performed by the fuzzy logic system. In some implementations, selection of the most significant attributes, parameters, variances, and/or rates of change is based on one or more different attribute selection approaches. These approaches may be (1) forward selection, which is starting with the most significant attributes and incrementally adding a next significant attribute until the model is stable; (2) backward elimination, which starts with all the attributes and exclude the non-significant attributes one by one until the model is stable; (3) a combination of forward selection and backward elimination; and (4) checking the significance of the attribute by statistical model (e.g., regression). In one embodiment, each attribute selection approach may give a subset of significant attributes. The attributes that are not shown to be significant by one or more of the attribute selection approaches may be excluded from the model. Weights may be assigned to each selected attribute based on the respective attribute's level of contribution to determining a measure of quality for MRI scans. For examples, the weights may be assigned according to a machine learning algorithm as described above. In an example embodiment, the assessment computing entity 100 may be a node of the neural network, deep net, network and/or the like comprising the fuzzy logic system. For example, the weights assigned according to the machine learning algorithm may be stored (e.g., in volatile memory 215 and/or non-volatile memory 210) such that they are accessible to the processing element 205 for determining the quality of measurement for the received data set.

In an example embodiment, the weights used to determine a quality of measurement may be determined for a particular type of scan. For example, the weights used to determine a quality of measurement for data corresponding to a task-based MRI may be different from the weights used to determine a quality of measurement for data corresponding to a resting state MRI, in an example embodiment. For example, in one embodiment, a set of weights used to determine a quality of measurement may correspond to a particular experimental design, scan type, and/or the like.

The process 500 may end with the optional step 516 shown in phantom. The process 500 may continue with filtering one or more potential reasons that cause data degradation (MRI scan quality degradation) based on the determined signal to noise ratio, signal to fluctuation noise ratio signal to ghost ratio, global intensity average, and variance for the four-dimensional data set (516). For example, the assessment computing entity 100 may determine that radio frequency (RF) interference is not responsible for an MRI scan classified as bad or low quality. Alternatively, the assessment computing entity 100 may determine that radio frequency (RF) interference is responsible for an MRI scan classified as bad or low quality. Accordingly, a user may take the necessary steps to improve the quality of the MRI scan.

In an example embodiment, a combination of the processes 400 and 500 may be performed. For example, the combined process may be generally performed by the assessment computing entity 100. For example, a set of data may be received as in steps 402 and 502. In an example embodiment, the set of data may be received in real time, near real time, as the scan is being performed, and/or the like. In an example embodiment, a combination of at least some of steps 404, 504, 506, 508, 510, and 512 may be performed such that one or more attributes, parameters, variances, and/or rates of change are determined. The one or more attributes, parameters, variances, and/or rates of change may then be used to determine a quality of measurement corresponding to the received set of data, such as in steps 408 or 514. The quality of measurement may then be classified (e.g., good/satisfactory, marginal/ok/fair, or poor/unsatisfactory) and a notification and/or alert may be provided to the appropriate physicians, medical personnel, and/or patients. In an example embodiment, the notification and/or alert may be provided in real time, near real time, as the scan is being performed, and/or the like.

FIG. 6 illustrates an example user interface 600 that may be provided to a physician or medical personnel. In particular, the user interface 600 provides the physician or medical personnel with one or more graphical representations of one or more attributes, parameters, variances, and/or rates of change and how such attributes, parameters, variances, and/or rates of change have evolved throughout the scan. In particular, the user interface 600 comprises a classification indicator 602. For example, the classification indicator 602 allows the physician or medical personnel a simple indication of the quality of measurement of the data set being obtained. For example, the illustrated classification indicator 602 shows a red block about the word "bad," indicating that the quality of the data being obtained is poor and/or unsatisfactory. The classification indicator 602 may then be used by the physician or medical personnel to make a decision during the scan to end the scan, restart the scan, and/or the like such that valuable scanner time is not wasted. In an example embodiment, the assessment device 100 and/or user device 110 may display and/or cause display of the user interface 600.

FIGS. 7A-7C depict an exemplary output metrics specifying various data measurements for MRI scans quality assessments. FIG. 7A-7C depict data sets associated with scans that are deemed satisfactory/high quality, potentially satisfactory/average quality, and non-satisfactory/low quality respectively. As shown, FIG. 7A has the lowest variance fluctuations and therefore is associated with a highest quality scan. Similarly, FIG. 7C depicts the highest variance fluctuations and therefore is associated with the lowest quality scan. The variance fluctuations of the FIG. 7B is in between those of FIG. 7A and FIG. 7C. As described above the metrics displayed in FIGS. 7A-7C may be use for MRI quality assessments.

IV. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer implemented method for providing real time quality monitoring of a magnetic resonance imaging (MRI) scan, the method comprising:
  receiving data associated with an MRI scan of a particular patient, the data being sequential MRI data associated with various times;
  determining a rate of change of the sequential data with reference to the various times, wherein determining the rate of change comprises determining a temporal derivative of the sequential data;
  determining whether the rate of change of the sequential data meets a first configurable threshold;
  determining whether the rate of change of the sequential data meets a second configurable threshold; and
  classifying the sequential data based on whether the rate of change of the sequential data meets the first and second configurable thresholds.

2. The method of claim 1, wherein the configurable threshold is proportional to a variance of the sequential data.

3. The method of claim 1, further comprising responsive to determining that the rate of change of the sequential data is less than the first configurable threshold, classifying the sequential data as satisfactory data.

4. The method of claim 1, further comprising responsive to determining that the rate of change of the sequential data exceeds the second configurable threshold, classifying the sequential data as non-satisfactory data.

5. The method of claim 1, further comprising responsive to determining that the rate of change of the sequential data exceeds the first configurable threshold and is less than the second configurable threshold, classifying the sequential data as potentially-satisfactory data.

6. The method of claim 1, further comprising providing to a first user device the classification of the sequential data for display on the first user device.

7. The method of claim 1, wherein the classification is provided in real-time.

8. A computer implemented method for providing real time quality monitoring of a magnetic resonance imaging (MRI) scan, the method comprising:
  receiving a three dimensional data set, the three dimensional data set representing a plurality of intensity measurements, each intensity measurement being associated with a time and a spatial location; and
  determining, a measure of quality for the received three-dimensional data set based on one or more parameters, wherein determining the one or more parameters comprises (a) determining a temporal derivative of the intensity measurements, (b) determining a spatial derivative of the intensity measurements, and (c) determining a variance for the three dimensional data set.

9. The method of claim 8, wherein determining the one or more parameters further comprises determining a signal to noise ratio for the three dimensional data set.

10. The method of claim 8, wherein determining the one or more parameters further comprises determining a signal to fluctuation noise ratio for the three dimensional data set.

11. The method of claim 8, wherein determining the one or more parameters further comprises determining a signal to ghost ratio for the three dimensional data set.

12. The method of claim 8, wherein determining the one or more parameters further comprises determining a global intensity average for the three dimensional data set.

13. The method of claim 8, wherein determining the one or more parameters further comprises determining a measure of movement of a patient receiving an MRI scan associated with the three dimensional data set.

14. The method of claim 8, further comprising filtering one or more potential reasons that cause data degradation based on the determined parameters.

15. The method of claim 8, further comprising determining one or more potential reasons that cause data degradation based on the determined parameters.

16. An apparatus comprising at least one processor, at least one non-transitory memory, and a communications interface coupled to a magnetic resonance imaging (MRI) scanning device, the at least one memory storing computer program code, the computer program code and memory, with the at least one processor, configured to:

receive data associated with an MRI scan of a particular patient, the data being sequential MRI data associated with various times;

determine a rate of change of the sequential data with reference to the various times wherein determining the rate of change comprises determining a temporal derivative of the sequential data;

determine whether the rate of change of the sequential data meets a first configurable threshold;

determine whether the rate of change of the sequential data meets a second configurable threshold; and classify the sequential data based on whether the rate of change of the sequential data meets the first and second configurable thresholds.

\* \* \* \* \*